United States Patent [19]
Gombotz et al.

[11] Patent Number: 5,451,411
[45] Date of Patent: Sep. 19, 1995

[54] METHODS AND COMPOSITIONS FOR THE ORAL DELIVERY OF THERAPEUTIC AGENTS

[75] Inventors: Wayne R. Gombotz, Kirkland, Wash.; Russell J. Mumper, Greenville, N.C.; Allan S. Hoffman, Seattle; Lisa S. Bouchard, Renton, both of Wash.

[73] Assignees: University of Washington, Seattle, Wash.; Bristol Myers Squibb Company, New York, N.Y.

[21] Appl. No.: 138,367

[22] Filed: Oct. 15, 1993

[51] Int. Cl.⁶ .......................... A61K 38/18; A61K 9/62
[52] U.S. Cl. ...................................... 424/499; 424/400
[58] Field of Search ...................... 514/772.6; 424/499

[56] References Cited

U.S. PATENT DOCUMENTS

| | | | |
|---|---|---|---|
| 4,740,365 | 4/1988 | Yukimatsu et al. | 424/435 |
| 4,822,534 | 4/1989 | Lenaki et al. | 264/4.3 |
| 4,923,645 | 5/1990 | Tsang et al. | 264/4.3 |
| 4,933,185 | 6/1990 | Wheatley et al. | 424/461 |
| 5,288,503 | 2/1994 | Wood et al. | 424/497 |

FOREIGN PATENT DOCUMENTS 1215922 12/1986 Canada ................................ 195/34.1

OTHER PUBLICATIONS

Goosen, M. F. A. et al., "Optimization of Microencapsulation Parameters: Semipermeable Microcapsules as a Bioartificial Pancreas," *Biotech. Bioeng.* 27:146–150 91985).

Kim, C.-K. and Lee, E.-J., "The controlled release of blue dextran from alginate beads," *Int. J. Pharm.* 79:11–19 (1992).

Pepperman, A. B. et al., "Alginate controlled release formulations of metribuzin," *J. Cont. Rel.* 17:105–111 (1991).

Pfister, G. et al., "Release Characteristics of Herbicides from Ca Alginate Gel Formulations," *J. Cont. Rel.* 3:229–233 (1986).

Katchalsky, A., "Counter-ion Fixation in Alginates," *J. Chem. Soc.* 1028:5198–5204 (1961).

Singh, O. N. and Burgess, D. J., "Characterization of Albumin–Alginic Acid Complex Coacervation," *J. Pharm. Pharmacol.* 41:670–673 (1989).

Chickering, D. et al., "A Tensile Technique to Evaluate the Interaction of Bioadhesive Microspheres with Intestinal Mucosa," *Proc. Int. Symp. Cont. Rel. Bio. Mater.* 19:88–89 (1992).

Segi, N. et al., "Interaction of Calcium–Induced Alginate Gel Beads with Propranolol," *Chem. Pharm. Bull.* 37(11):3092–3095 (1989).

Stockwell, A. F. et al., "In Vitro Evaluation of Alginate Gel Systems as Sustained Release Drug Delivery Systems," *J. Contr. Rel.* 3:167–175 (1986).

Bhakoo, M. et al., "Release of Antibiotics and Antitumour Agents from Alginate and Gellan Gum Gels," *Proc. Int. Symp. Cont. Rel. Bio. Mater.* 18:441–442 (1991).

Downs, E. C. et al., "Calcium Alginate Beads as a Slow-Release System for Delivering Angiogenic Molecules In Vivo and In Vitro," *J. Cell. Phys.* 152:422–429 (1992).

(List continued on next page.)

*Primary Examiner*—Thurman K. Page
*Assistant Examiner*—Peter F. Kulkosky
*Attorney, Agent, or Firm*—Christensen O'Connor Johnson & Kindness

[57] ABSTRACT

Alginate beads are employed as a site specific oral delivery system for cationic therapeutic agents, such as TGF-$\beta_1$, designed to target the agents to the luminal side of the small intestine. Improved delivery of bioactive material is obtained by: 1) incorporating selected polyanions in the alginate beads to shield the cationic therapeutic agent from interaction with alginate and/or 2) acid treating alginate beads containing the therapeutic agents to reduce the molecular weight of alginate and its interaction with the agents. Enhanced bioactivity of therapeutic agents released from the alginate is attributed to the ability of polyacrylic acid to shield the agents from interaction with lower molecular fragments of acid treated alginate.

10 Claims, 6 Drawing Sheets

OTHER PUBLICATIONS

Edelman, E. R. et al., "Controlled and modulated release of basic fibroblast growth factor," *Biomaterials* 12:619–625 (1991).

Assoian, R. K. et al., "Transforming Growth Factor-$\beta$ in Human Platelets," *J. Biol. Chem.* 258(11):7155–7160 (1983).

Sporn, M. B. et al., "Transforming Growth Factor-$\beta$: Biological Function and Chemical Structure," *Science* 233:532–534 (1986).

Massague, J., "The TGF-$\beta_1$ Family of Growth and Differentiation Factors," *Cell* 49:437–438 (1987).

Haug, A. et al., "Studies on the Sequence of Uronic Acid Residues in Alginic Acid," *Acta Chem. Scand.* 21(3):691–704 (1967).

Haug, A. and Larsen, B., "Quantitative Determination of the Uronic Acid Composition of Alginates," *Acta Chem. Scand.* 16(8):1908–1918 (1962).

Haug, A. et al., "The Degradation of Alginates at Different pH Values," *Acta. Chem. Scand.* 17(5):1466–1468 (1963).

Haug, A. and Larsen, B., "The Solubility of Alginate at Low pH," *Acta. Chem. Scand.* 17(6):1653–1662 (1963).

Bodmeier, R. and Paeratakul, O., "Spherical Agglomerates of Water–Insoluble Drugs," *J. Pharm. Sci.* 78(11):964–967 (1989).

Berth, G., "Methodical aspects of characterization of alginate and pectate by light scattering and viscometry coupled with GPC," *Carb. Poly.* 19:1–9 (1992).

Lehr, C.-M. et al, "Effects of the Mucoadhesive Polymer Polycarbiphil on the Intestinal Absorption of a Peptide Drug in the Rat," *J. Pharm. Pharmacol.* 44:402–407 (1992).

Duchêne, D. and Ponchel, G., "Principle and investigation of the bioadhesion mechanism of solid dosage forms," *Biomaterials* 13(10):709–714 (1992).

Smart, J. D., "An in vitro assessment of some mucosa–adhesive dosage forms," *Int. J. Pharm.* 73:69–74 (1991).

Gombotz, W. et al., "The Controlled Release of TGF-$\beta_1$ from Different Formulations for Wound Healing," *Proc. Int. Symp. Cont. Rel. Bio. Mater.*, 19:108–109 (1992).

Smidsrod, O. and Skjåk-Br k, G., "Alginate as immobilization matrix for cells," *Trends Biotech.* 8:71–78 (1990).

Martinsen, A. et al., "Alginate as Immobilization Material: I. Correlation between Chemical and Physical Properties of Alginate Gel Beads," *Biotech. Bioengin.* 33:79–89 (1989).

METHODS AND COMPOSITIONS FOR THE ORAL DELIVERY OF THERAPEUTIC AGENTS

FIELD OF THE INVENTION

The present invention relates to methods and compositions for the oral delivery of cationic proteins for therapeutic purposes. More particularly, the present invention relates to alginate systems including synthetic polymer additives for the delivery of therapeutic agents, such as TGF-$\beta_1$, in active form.

BACKGROUND OF THE INVENTION

Alginate is a copolymer of 1,4-linked $\beta$-D-mannuronic and $\alpha$-L-guluronic acid. It has the unique property of gel-formation in the presence of divalent actions such as calcium, and has been used to immobilize cells (M.F.A. Goosen et al., "Microencapsulation of Living Tissue and Cells," Canadian Patent 1,215,922 (1982)), as potential artificial organs (M.F.A. Goosen et al., "Optimization of Microencapsulation Parameters: Semipermeable Microcapsules as a Bioartificial Pancreas," *Biotech. Bioeng.* 27:146–150 (1985)), and as delivery systems for drugs (C.K. Kim and E.J. Lee, "The Controlled Release of Blue Dextran from Alginate Beads," *Int. d. Pharm.* 79:11–19 (1992)), pesticides (A.B. Pepperman et al., "Alginate Controlled Release Formulations of Metribuzin," *J. Cont. Rel.* 17:105–112 (1991)), and herbicides (G. Pfisteret al., "Release Characteristics of Herbicides from Ca Alginate Gel Formulations," *J. Cont. Rel.* 3:229–233 (1986)). The gelation and cross-linking of alginate with calcium are due to the stacking of guluronic acid (G) blocks with the formation of 'egg-box' junctions (A. Katchalsky et al., "Counter-Ion Fixation in Alginates," *J. Chem. Soc.* :5198–5204 (1961)). Thus, the dropwise addition of an alginate solution into a stirred solution of calcium chloride and drug will result in the encapsulation of the drug within an alginate hydrogel bead containing up to 95% water (M.F.A. Goosen et al., "Microencapsulation of Living Tissue and Cells," Canadian Patent 1,215,922 (1982)).

Purified alginate is non-toxic when taken orally, biodegradable and bioacceptable (C.K. Kim and E.J. Lee, "The Controlled Release of Blue Dextran from Alginate Beads," *Int. J. Pharm.* 79:11–19 (1992); O.N. Singh and D.J. Burgess, "Characterization of Albumin-Alginic Acid Complex Coacervation," *J. Pharm. Pharmacol.* 41:670–673 (1989)). Alginate has also been tested clinically as a component of synthetic pancreatic beta cells (as artificial pancreatic material). In addition, alginate has been found to have a protective effect on the mucous membranes of the upper gastrointestinal tract (D. Koji etal., "Pharmacological Studies of Sodium Alginate. I. Protective Effect of Sodium Alginate on Mucous Membranes of Upper-Gastrointestinal Tract," *Yakugaku Zasshi* 101:452–457 (1981)) and has been investigated as an bioadhesive (D. Chickering et al., "A Tensile Technique to Evaluate the Interaction of Bioadhesive Microspheres with Intestinal Mucosa," *Proc. Int. Symp. Cont. Rel. Bio. Mater.* 19:88–89 (1992)). Alginate beads have been used as a potential delivery system for many cationic drugs such as propranolol (N. Segi et al., "Interaction of Calcium-Induced Alginate Gel Beads with Propranolol," *Chem. Pharm. Bull.* 37:3092–3095 (1989)) chlorpheniramine (A.F. Stockwell et al., "In Vitro Evaluation of Alginate Gel Systems as Sustained Release Drug Delivery Systems," *J. Contr. Rel.* 3:167–175 (1986)), theophylline (M. Bhakoo et al., "Release of Antibiotics and Antitumour Agents from Alginate and Gellan Gum Gels," *Proc. Int. Symp. Cont. Rel. Bio. Mater.* 18:441–442 (1991)), and protein growth factors such as basic fibroblast growth factor (bFGF) (E.C. Downsetal., "Calcium Alginate Beads as a Slow-Release System for Delivering Angiogenic Molecules In Vivo and In Vitro," *J. Cell. Phys.* 152:422–429 (1992), E.R. Edelman et al., "Controlled and Modulated Release of Basic Fibroblast Growth Factor," *Biomaterials* 12:619–625 (1991)). The mucosal epithelium of the intestine is in a continuously dynamic state known as "epithelial renewal" (G.L. Eastwood, *Gastroenterology* 72:962 (1980)) where undifferentiated stem cells from the proliferative crypt zone divide, differentiate and migrate to the luminal surface where, once terminally differentiated, are sloughed from the tips of the villi. The turnover of a crypt-villus cell population is rapid and occurs every 24–72 h (H. Cheng and C. Leblond, *Am. J. Anat.* 141:461 (1974)). Continuous exfoliation of the cells at the viiius tip is counterbalanced by ongoing proliferation in the crypt so that the net intestinal epithelial mass remains relatively constant. The multifactorial regulation of this balance is not fully understood (*Physiology of the Gastrointestinal Tract*, L.R. Johnson, Ed. (Raven Press, New York), pp. 69–196 (1987)). It may, however, be accomplished through the combined integration of key peptide growth factors and constituents of the extracellular matrix (D.K Podolsky, *Am. J. Physiol.* 264:G1.79 (1993)). Transforming growth factor beta (TGF-$\beta$), an acid and heat stable, disulfide-linked, homodimeric 25 kD protein is present in most tissues and is known to play an important regulatory role in cell proliferation, migration, and differentiation (R.K. Assoian et al., *J. Biol. Chem.* 258:7155 (1983); M.B. Spornet al., *Science* 233:532 (1986); J. Massague, *Cell* 49:437 (1987)). TGF-$\beta$ has been shown to inhibit the growth of many cells of epithelial origin, including human and rodent derived intestinal cells (M. Kurokawa et al., *Biochem. Biophys. Res. Comm.* 142:775 (1987) and J.A. Barnard et al., *Proc. Natl. Acad. Sci. USA* 86:1578 (1989)). TGF-$\beta$ mRNA is expressed in gastrointestinal epithelium (R.P. McCabe et al., *Clin. Immunol. Immunopathol.* 66:52 (1993)) and the non-transformed rat jejunal crypt cell line (IEC-6) express TGF-$\beta$mRNA (S. Koyama and D.K. Podolsky, *J. Clin. Invest.* 83:1768 (1989)) and secretes latent TGF-$\beta$ (M. Kurokawa et al., *Biochem. Biophys. Res. Comm.* 142:775 (1987) and J.A. Barnard et at., *Proc. Natl. Acad. Sci. USA* 86:1578 (1989)).

The rapidly proliferating epithelium of the gastrointestinal tract is extremely sensitive to cytotoxic drugs widely used in chemotherapy of cancer. The tolerable dose of these drugs is limited and often suboptimal dosages have to be used because of gut toxicity. Trials in cancer patients receiving chemotherapeutic agents have demonstrated a variety of gastrointestinal complications ranging from dyspepsia to life threatening hemorrhage from mucosal ulcerations. As many as 50% of lung cancer patients enrolled in a cisplatin plus etoposide combination chemotherapy trial were unable to complete the treatment protocol because of excessive acute gastrointestinal toxicity (S. Sartori etal., *Oncology* 48:356 (1991)). Sequential chemotherapeutic protocols using cytosine arabinoside, floxuridine and mitomycinC induced gastrointestinal toxic alterations characterized by surface and glandular epithelial atypia, immaturity and necrosis (R.E. Slavin et al., *Cancer* 42:1747 (1978))

often leading to severe systemic infections by streptococci, candida and other pathogens.

Certain growth factors exhibit gastroprotective activities and enhance the healing of gastric lesions (S.J. Konturek et al., *Scand. J. Gastroenterol.* 27:649 (1992)). Since TGF-$\beta$ inhibits the proliferation of intestinal epithelial cells, it would be highly desirable to have access to a suitable system for the oral delivery of TGF-$\beta_1$ to the gastrointestinal tract in active forms and/or for the delivery of TGF-$\beta_1$ or other cationic drugs to other delivery target areas. Due to its nontoxic nature, an alginate-based delivery system would appear useful for this purpose.

However, for encapsulation of cationic drugs, such as TGF-$\beta_1$, strong complexation between alginate and the cationic drug leads to increased drug loadings into beads but decreased diffusion rates out of beads. In addition, several authors observed competition between calcium ions and the cationic drug for available carboxylic acid sights on alginate (N. Segi et al., "Interaction of Calcium-Induced Alginate Gel Beads with Propranolol," *Chem. Pharm. Bull.* 37:3092–3095 (1989); A.F. Stockwell et al., "In Vitro Evaluation of Alginate Gel Systems as Sustained Release Drug Delivery Systems," *J. Contr. Rel.* 3:167–175 (1986)).

Thus, while alginate beads have been known in the an as potential delivery systems for various therapeutic drugs, it has been found that complex interaction between alginate and cationic therapeutic agents prevents release of the therapeutic agents from the alginate beads in active form. Accordingly, there is a strong need in the art for improved alginate delivery systems for cationic therapeutic agents.

SUMMARY OF THE INVENTION

It has now been discovered that alginate can be used as an oral delivery system for cationic therapeutic agents by providing unique bead fabrication conditions coupled with the co-encapsulation of stabilizing polyanionic additives that protect the therapeutic agent from inactivation and deliver the agent with reproducible and desirable kinetics. The methods and compositions of the invention provide an oral controlled release system that targets therapeutic agents to the luminal side of the intestines (e.g., to the duodenum and jejunum).

In one aspect, the present invention provides a method for preparing alginate beads for delivery of cationic therapeutic agents to humans or nonhuman mammals in need of treatment, comprising forming the beads in the presence of the therapeutic agent and an anionic protective polymer, and then incubating the beads under acidic conditions to an extent sufficient to enhance release of the therapeutic agent from the beads. The resulting compositions have been surprisingly found to readily release high levels of cationic therapeutic agents in active form.

BRIEF DESCRIPTION OF THE DRAWINGS

The foregoing aspects and many of the attendant advantages of this invention will become more readily appreciated as the same becomes better understood by reference to the following detailed description, when taken in conjunction with the accompanying drawings, wherein:

FIG. 1A represents a cured alginate bead containing TGF-$\beta_1$; FIG. 1B represents a cured and acid treated alginate bead containing TGF-$\beta_1$; FIG. 1C represents a cured alginate bead containing PAA and TGF-$\beta_1$; and FIG. 1D represents a cured and acid treated alginate bead containing PAA and TGF-$\beta_1$. The symbol (■) in FIGS. 1A–1D represents a calcium cross link;

DETAILED DESCRIPTION

Figure 1A:
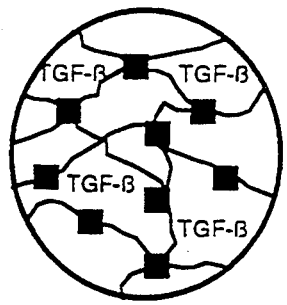
FIGS. 1A–1D are pictorial representations of alginate beads when placed in PBS, pH 7.4 at 37° C.
Figure 1A:
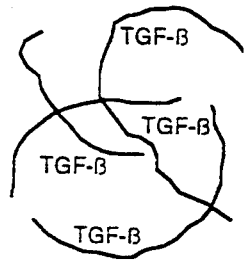

In accordance with the invention, a mixture is formed of alginate, the cationic therapeutic agent and the anionic protective polymer, and then the mixture is formed into beads using procedures known in the art. For example, the mixture may be pushed through a syringe, e.g., fitted with a 25–50 G needle, into a solution containing a multivalent cation at neutral pH. To obtain small beads of uniform size, the alginate mixture is preferably introduced into the cationic solution by applying constant and even pressure to the syringe plunger while swirling the cationic solution. Alternatively, the mixture may be sprayed into the multivalent cationic solution through a nozzle or other orifice adapted to disperse the mixture into droplets. Upon contact with the cationic solution, multivalent cation cross-linking of the alginate occurs resulting in bead formation. The beads may then be recovered and washed for subsequent analysis or use. For purposes of convenience, low cost and biocompatibility, the multivalent cation is preferably $Ca^{++}$, although other multivalent cations, preferably divalent cations such as $Pb^{2+}$, $Cu^{2+}$, $Cd^{2+}$, $Ba^{2+}$, $Sr^{2+}$, $Co^{2+}$, $Ni^{2+}$, $Zn^{2+}$ or $Mn^{2+}$, or trivalent cations such as $Al^{3+}$ or $Fe^{3+}$, may also be employed. In a presently preferred embodiment, the alginate mixture is preferably introduced into a $CaCl_2$ solution to obtain bead formation.

Anionic protective polymers useful in the practice of the invention include acidic polymers, such as polyacrylic acid (PAA). In order to obtain optimal release of the therapeutic agent from the alginate beads in active form, the polyacrylic acid will preferably have a molecular weight in the range of about 10 to about 250 kDa, more preferably from about 75 to about 150 kDa. A sufficient amount of polyacrylic acid is preferably incorporated into the prebead mixture to protect the cationic therapeutic agent from ionic interaction with the alginate. However, too large an amount of polyacrylic acid will prevent bead formation. Accordingly, the prebead mixture will preferably comprise an alginate:PAA ratio of from 75:2 to 75:10, more preferably from 75:5 to 75:10.

To enhance release of the therapeutic agent from the alginate beads, the beads are subjected to acid treatment prior to use. The beads may be acid treated by incubating the beads at a pH from 1–4, more preferably from 1–2, for a sufficient period of time to enhance release of the therapeutic agent from the beads. Generally, acid treatment times of at least 0.25 hours will be sufficient to obtain the desired effect, although the beads may be acid treated for up to 24 hours or longer, if desired, without significantly further effecting their dissolution profiles or therapeutic agent release rates. For example, the beads may be incubated in an HCl solution at 37° C. and pH 1 for 30 minutes to obtain satisfactory acid treatment of the beads.

The method and compositions of the invention are particularly suited for the delivery of cationic protein therapeutic agents to human or nonhuman mammal subjects. As illustrated in detail in the examples, the methods and compositions are highly effective for the release of active TGF-$\beta_1$, Oncostatin-M and Amphiregulin, although other cationic therapeutic agents may be equally employed in the practice of the invention.

Figure 1B:
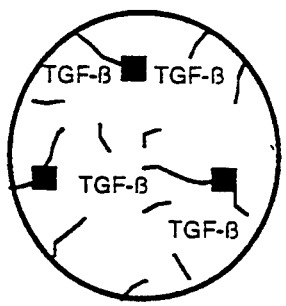
Figure 1B:
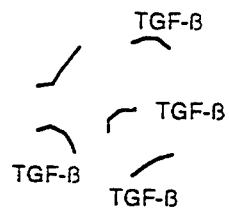
Figure 1C:
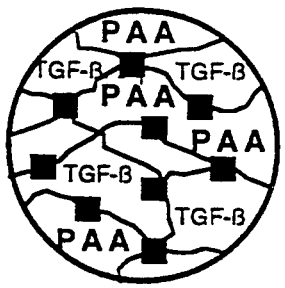
Figure 1C:
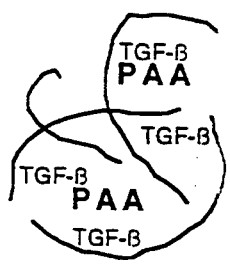
Figure 1D:
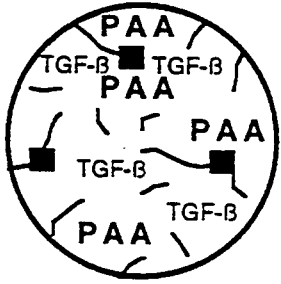
Figure 1D:
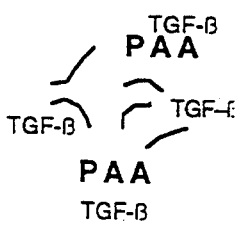

Although not wanting to be bound by any particular theory of operation, it is believed that the incorporation of polyacrylic acid (PAA) in the prebead alginate mixture results in significant protection of the cationic therapeutic agent from ionic interaction with alginate in a subsequently formed bead. In addition, acid treatment of the formed bead reduces crosslinking in the alginate matrix and highly facilitates release of the therapeutic agent in active form from the beads. This is pictorially depicted in FIG. 1 in which alginate beads release the therapeutic agent TGF-$\beta_1$ upon incubation in phosphate-buffered saline solution (PBS). FIG. 1A depicts a cured alginate bead containing TGF-$\beta_1$, but no polymeric protective agent. FIG. B depicts a cured and acid treated alginate bead containing TGF-$\beta_1$. As shown in FIGS. 1A and 1B, a limited immunoreactivity of released TGF-$\beta_1$ is obtained due to ongoing interaction of the therapeutic agent with the alginate. Although the acid treatment process (shown in FIG. 1B) results in alginate with a reduced molecular weight, a strong alginate interaction with the TGF-$\beta_1$ remains. A cured alginate bead containing PAA and TGF-$\beta_1$ is depicted in FIG. 1C, while a cured and acid treated alginate bead containing PAA and TGF-$\beta_1$ is depicted in FIG. 1D. The ability of PAA to shield alginate from TGF-$\beta_1$ (depicted in FIG. 1C) results in a significantly increased immunoreactivity of released TGF-$\beta_1$, even in beads which are not acid treated. However, the highest degree of immunoreactivity of released TGF-$\beta_1$ results from the encapsulation of PAA as an additive plus the utilization of the acid treatment process (as depicted in FIG. 1D), due to PAA shielding of the TGF-$\beta_1$ from acid treated alginate fragments.

The alginate bead compositions of the invention are particularly suited for the formation of sustained release capsules for the oral delivery of cationic therapeutic agents. In the use of the compositions of the invention, no therapeutic agent is released in the low pH environment of the stomach. Rather, therapeutic agent release occurs in a relatively linear fashion in the more neutral pH environment of the intestines. In addition to protecting the therapeutic agent from ionic interaction with alginate, the polyacrylic acid of the invention may additionally serve as a bioadhesive to provide sustained delivery of TGF-$\beta_1$ to enterocytes. These and other aspects of the invention may be better understood in connection with the following illustrative examples.

EXAMPLES

Materials

Unless otherwise indicated, the following materials were employed in the Examples described below: TGF-$\beta_1$ (1 mg/mL in 5 mM HCl) was obtained from Bristol-Myers Squibb (Seattle, WA). Low viscosity sodium alginate from *Macrocystis pyrifera* kelp (LVM from Sigma, St. Louis, MO; $F_G$=43%; Mw=80 kDa), calcium chloride, sodium chloride, sodium carboxymethyl cellulose (high viscosity), and polyacrylic acid (PAA) polymers (Mw=2, 5, 90, 250, 450, and 750 kDa) were purchased from Aldrich (Milwaukee, WI). Potassium chloride, 2-mercaptoethanol 98%, and chloramine-T hydrate 98% were also obtained from Aldrich. Other sodium alginates including low viscosity, high guluronic content ($F_G$=68%; Mw=170–270 kDa), medium viscosity, high guluronic content ($F_G$=68%; Mw=170–270 kDa), and low viscosity, high mannuronic (M) content (FM=65%; Mw=270–350 kDa) were supplied by Protan (Woodinville, WA). L-glutamic acid, L-aspartic acid, and sodium poly-L-aspartic acid (PLLA) (Mw=13 kDa), and poly-L-Lysine (PLL) (Mw=123 kDa; Mw/Mn=1.32) were purchased from Sigma (St. Louis, MO). Phosphate buffered saline (PBS; pH 7.4), citrate phosphate buffer (CPB), and HCl solutions (pH 1.0, 2.0, 3.0, and 4.0) were prepared fresh as needed. All water used was distilled and deionized.

EXAMPLE 1

Encapsulation of TGF-$\beta_1$ in Untreated and Acid Treated Alginate beads

Radioiodination of TGF-$\beta_1$: Radioiodination of TGF-$\beta_1$ was completed in a 3.0-mL Eppendorf tube using a modified chloramine-T method (A. Tuong et al., "Site Specific Radioiodination of Recombinant Himdin," *Annal. Biochem.* 189:186–191 (1990)). To TGF-$\beta_1$ (1 mg/1 mL) in 5 mMHCl, 10 μL of carrier-free Na$^{125}$I (1.0 mCi) was added and mixed for 5 minutes. 100 μL of 0.1% chloramine-T was then added and, after vortexing for 60 seconds, the reaction was stopped by the addition of 100 μL of aqueous 0.1% mercaptoethanol followed by 100 μL of 0.1% KCl. $^{125}$I-TGF-$\beta_1$ was diluted by adding 1.2 mL of citrate phosphate buffer (CPB), pH 2.6.

Free $^{125}$I was separated from $^{125}$I-TGF-$\beta_1$ by gel filtration on a prepacked Sephadex G-25 column from Pharmacia (Uppsala, Sweden) preequilibrated with CPB. Twenty fractions of 0.5 mL each were collected, and aliquots were counted for activity using a γ-scintillation counter (Model 1185 GammaTrac; Tm Analytic; Elk Grove Village, IL). Separated $^{125}$I-TGF-$\beta_1$ (S.A.=0.72 nCi/ng or 187 ng/μL was stored at 4° C. in 1.5 mL-Eppendofftubes.

Formation of Sodium Alginate-TGF-$\beta_1$ Prebead Mixture: 50 μL of TGF-$\beta_1$ or $^{125}$I-TGF-$\beta_1$ (50 μg) was transferred to a 1.5 mL-Eppendorf tube, and water (0–1100 μL) was added to dilute the TGF-$\beta_1$. Next, 250 or 500 μL (3.75 or 7.5 mg) of a 1.5% w/v sodium alginate solution was added to produce a clear prebead complex mixture. Prebead mixtures containing additives were made by first adding the additives (100–1000 μL of a 0.1% w/v solution) to TGF-$\beta_1$, followed by water and alginate. The volume of water added to all mixtures was adjusted so that the final prebead volume was always 1.5 mL. For the release studies described below, the TGF-$\beta_1$ was combined with $^{125}$I-TGF-$\beta_1$ (400,000 cpm) prior to mixing.

Formation of Beads: 1.5 mL of the prebead mixture was drawn into a syringe equipped with a 30 G needle. The mixture was forced slowly through the needle placed approximately 2–4 cm above a 10 mL calcium chloride solution in a 30 mL polypropylene beaker. The calcium chloride solution (1.0% w/v) was stirred rapidly using a magnetic stirrer. The cure time of the alginate beads in calcium chloride was 10 minutes. At the completion of the curing process, calcium chloride was drained and the beads were washed 3 times with 10 mL water to remove adhered calcium. If $^{125}$I-TGF-$\beta_1$ was incorporated in the beads, calcium chloride was retained and counted for activity along with the 1.5 mL-Eppendoff tube to determine the % encapsulation of TGF-$\beta_1$ in beads.

To determine the encapsulation efficiency of TGF-$\beta_1$ in alginate beads, the cpm of the beads containing $^{125}$I-TGF-$\beta_1$ was determined and compared with the cpm of $^{125}$I-TGF-$\beta_1$ remaining in the calcium chloride solution and container following bead formation and removal. The percent encapsulation was calculated as [(radioactivity in the beads/total radioactivity in the beads and calcium chloride solution)]×100. Encapsulation efficiencies of TGF-$\beta_1$ were greater than 97.5% (48.75 μg TGF-$\beta_1$) for most preparations as long as the prebead mixtures were made in polypropylene tubes. The use of glass vials resulted in the loss of more than 98% of the TGF-$\beta_1$, presumably due to binding of TGF-$\beta_1$ to the glass. Greatly reduced encapsulation efficiencies resulted if lower concentrations of alginate or calcium chloride were used in the preparations due to the formation of unspherical beads or even gelled alginate.

The high encapsulation efficiency of the TGF-$\beta_1$ (pI 9.82) in alginate was most likely due to strong interaction between the positively charged growth factor and the negatively charged polysaccharide. However, previous authors reported that similarly charged bFGF (pI 9.6) could only be entrapped with 7–19% (E.C. Downset al., "Calcium Alginate Beads as a Slow-Release System for Delivering Angiogenic Molecules In Vivo and In Vitro," *J. Cell. Phys.* 152:422–429 (1992)) or less than 10% (E.R. Edelman et al., "Controlled and Modulated Release of Basic Fibroblast Growth Factor," *Biomaterials* 12:619–625 (1991)) encapsulation efficiencies using similar encapsulation techniques. Although TGF-$\beta_1$ and bFGF have similar charges at neutral pH, a much greater amount of TGF-$\beta_1$ was encapsulated in the alginate beads than bFGF encapsulation reported in the art. These results suggest that charge of the protein may not be the only factor that influences its ability to be encapsulated.

EXAMPLE 2

Release of Encapsulated TGF-$\beta_1$

Beads prepared in accordance with the procedure of Example 1 and containing 50 μg of $^{125}$I-TGF-$\beta_1$ in 3.75–7.5 mg (original weight of alginate) were transferred to 15.0 mL polypropylene tubes containing 13.0 mL of PBS or of 0.1 N HCl at 37° C. In some cases, 1% BSA was added to the release media. The polypropylene tubes were gently shaken using a orbital shaker (200 rotations/minutes). At selected times, 100 μL aliquots were taken and counted for radioactivity. Care was taken so that aliquots contained no beads or bead fragments. The cumulative $^{125}$I-TGF-$\beta_1$ released from the beads was calculated after correcting for volume changes. After 24 hours, the beads in 0.1 N HCl were transferred to PBS.

Figure 2:
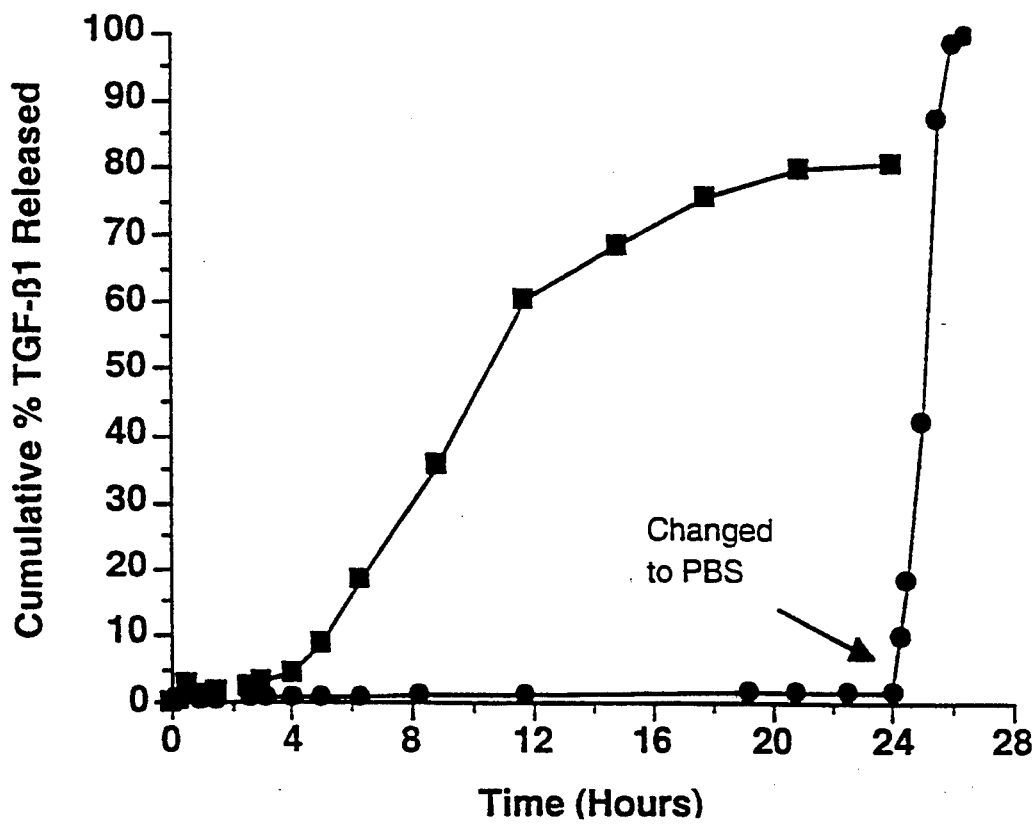
FIG. 2 is a graphical representation of the cumulative percent in-vitro release of $^{125}$I-TGF-$\beta_1$ at 37° C. in: PBS, pH 7.4 (shown in FIG. 1 as ■), and 0.1 N HCl, pH 1.0 transferred to PBS after 24 hours (shown in FIG. 1 as ●), determined as described in Example 2. Alginate beads (75:0 w/w) containing 50.0 μg of $^{125}$I-TGF-$\beta_1$ were cured in 1% CaCl$_2$ for 10 minutes.

Release profiles of $^{125}$I-TGF-$\beta_1$ from alginate beads in PBS and 0.1 N HCl are shown in FIG. 2. After a 4 hour lag period, $^{125}$I-TGF-$\beta_1$ was released in a continuous manner into PBS (■ in FIG. 2) reaching a plateau of 81% after 20 hours. After 24 hours, some undissolved and irregular alginate beads (containing 9.5 μg $^{125}$I-TGF-$\beta_1$) remained. Even after 72 hours, no further $^{125}$I-TGF-$\beta_1$ was released (not shown) suggesting that the $^{125}$I-TGF-$\beta_1$ remained tightly bound in the remaining alginate.

In comparison, alginate beads in 0.1 N HCl (● in FIG. 2) released essentially no $^{125}$I-TGF-$\beta_1$ in 24 hours. However, when alginate beads in 0.1 N HCl were transferred to PBS, the beads underwent extremely rapid swelling and dissolution, and 100% of the $^{125}$I-TGF-$\beta_1$ was released in 2.5 hours.

Acid Treatment of Beads: Alginate beads prepared according to the procedure of Example 1 and containing TGF-$\beta_1$ were placed in 13.0 mL of 0.1 N HCl at 37° C. for 0.25–24 hours to obtain lower and more soluble molecular weight fractions (A. Haug et al., "Studies on the Sequence of Uronic Acid Residues in Alginic Acid," Acta Chem. Scand. 21:691–704 (1967); A. Haug and B. Larsen, "Quantitative Determination of the Uronic Acid Composition of Alginates," Acta Chem. Scand. 16:1908–1918 (1962); A. Haug et al., "The Degradation of Alginates at Different pHValues," Acta. Chem. Scand. 17:1466–1468 (1963); A. Haug and B. Larsen, "The Solubility of Alginate at Low pH," Acta. Chem. Scand. 17:1653–1662 (1963)). After the acid treatment, the beads were removed and washed several times with phosphate buffered saline (PBS). The PBS wash was monitored with a pH meter to assure that the pH of the wash was 7.4.

The ability of released TGF-$\beta_1$ from both untreated and acid treated beads (as described above) to be recognized (bound) by a monoclonal antibody was assayed by ELISA as follows. An enzyme linked immunosorbent assay (ELISA) was used to quantitate the amount of immunoreactive TGF-$\beta_1$ released from the untreated (PBS) and acid treated (HCl) alginate beads. The ELISA was based on the ability of a mouse anti-TGF-$\beta_1$ monoclonal antibody, 1D11 (Bristol-Myers Squibb, Seattle, WA), to bind to the TGF-$\beta_1$ molecule. When the 1D11 antibody was coated on 96-well immunoassay plates it captured TGF-$\beta_1$ from the applied sample and standard solutions. Captured TGF-$\beta_1$ was then bound by biotinylated 1D11 antibody which in turn was bound by a horseradish peroxidase/avidin D conjugate (Vector Labs cat #A-2004). A color reaction occurred by adding a chromophore/substrate solution of 3,3',5,5'-tetramethylbenzidine in CPB containing hydrogen peroxide. The reaction was stopped with the addition of 1 N sulfuric acid and the A450 was determined by a plate reader. Concentrations of the unknown samples were quantified relative to a TGF-$\beta_1$ standard curve run on the same plate. The results are shown in the following Table 1:

TABLE 1

| % Binding Activity | |
|---|---|
| PBS | HCl |
| 0 | 14 |

The ELISA measured binding activity of released TGF-$\beta_1$ from alginate beads which were not acid treated (PBS) was 0%, whereas 14% binding activity was retained when the beads were acid treated in 0.1 N HCl. The ELISA assay is not indicative of bioactivity of the TGF-$\beta_1$, but it does provide information concerning changes in the conformation or structure of the protein. A reduction in ELISA binding activity indicates that the site on the molecule to which the monoclonal antibody binds has undergone some type of change. This change could be caused by protein denaturation, aggregation or masking of the binding site by another molecule. The ELISA data showed that acid treated alginate interacted with released TGF-$\beta_1$ to a smaller extent than untreated alginate. The decreased TGF-$\beta_1$-alginate interaction ultimately resulted in a greater retention of immunoreactivity.

EXAMPLE 3

Bead Swelling

It has been reported by previous authors that alginate beads in low pH do not swell or release their contents to any great extent (N. Segi et al., "Interaction of Calcium-Induced Alginate Gel Beads with Propranolol," Chem. Pharm. Bull. 37:3092–3095 (1989); R. Bodmeier and O. Paeratakul, "Spherical Agglomerates of Water-Insoluble Drugs," J. Pharm. Sci. 78:964–967 (1989)). However, the rapid swelling and releasing properties of acid treated alginate beads after being transferred to neutral pH has not previously been reported. Swelling studies of alginate beads alone (without incorporated TGF-$\beta_1$) in PBS (designated "Alg"), alignate beads with incorporated TGF-$\beta_1$ in PBS (designated "TGF"), and alignate beads with incorporated TGF-$\beta_1$ in 0.1 N HCl (designated "HCl") were conducted to gain insight in this unique property of the alginate beads. Alginate beads prepared according to Example 1, in PBS, without TGF-$\beta_1$ (■ in FIG. 3); in PBS with 50 μg of TGF-$\beta_1$ (● in FIG. 3); or with 50 μg of TGF-$\beta_1$ in 0.1 N HCl (pH 1.0) and transferred to PBS at 165 minutes (▲ in FIG. 3) were removed at selected time intervals and the average diameters of ten beads were determined with the use of a caliper.

Figure 3:
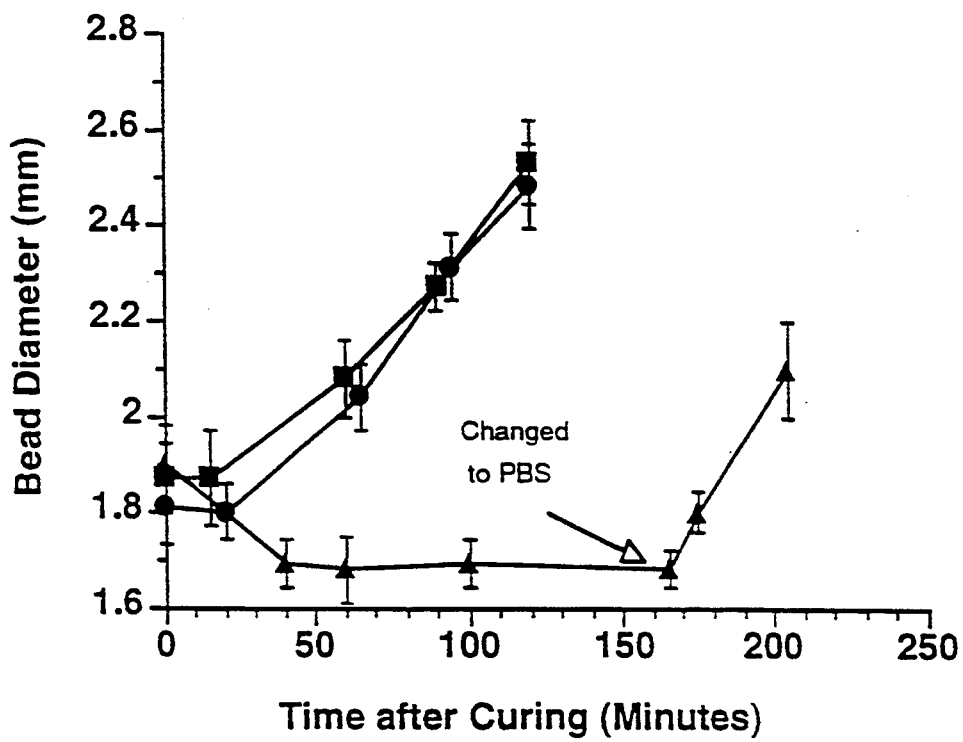
FIG. 3 is a graphical representation of swelling of alginate beads (75:0 w/w) at 37° C. for: Empty beads in PBS, pH 7.4 (shown as ■ in FIG. 2); Beads containing 50.0 μg TGF-$\beta_1$ in PBS (shown as ● in FIG. 2); and Beads containing 50 TGF-$\beta_1$ in 0.1 N HCl transferred to PBS at 165 minutes (shown as ▲ in FIG. 2), determined as described in Example 3. The error bars in FIG. 2 represent the standard deviation from the mean diameter of ten beads. All beads were cured in 1% CaCl$_2$ for 10 minutes.
Figure 4:
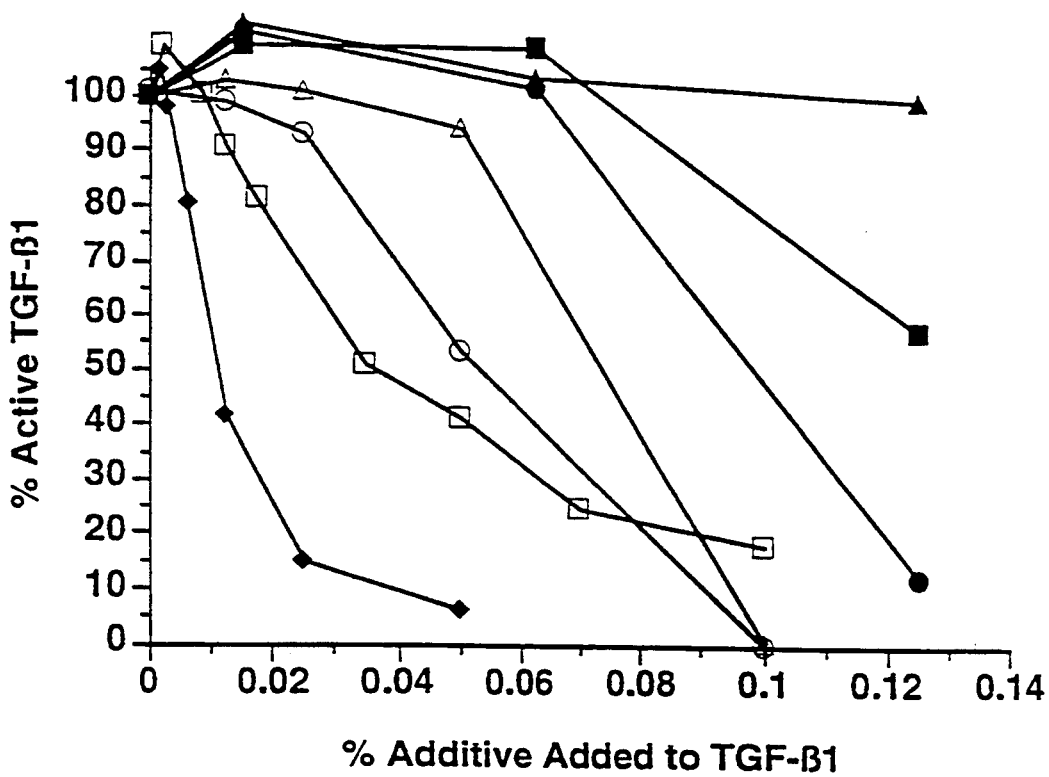
FIG. 4 is a graphical representation of the percentage of total TGF-$\beta_1$ released in immunoreactive form, as measured by ELISA immunoreactivity of released TGF-$\beta_1$, in the presence of additives (% w/v) in solutions containing no alginate determined as described in Example 5. The following additives were employed at the % w/v indicated in FIG. 4: glutamic acid (■), aspartic acid (●), poly-L-aspartic acid (PLAA, ▲), sodium carboxymethyl cellulose (NaCMC, high viscosity, ◆), polyacrylic acid (Mw=750 kDa, □), PAA (90 kDa, ○), and PAA (2 kDa, △)

As shown in FIG. 3, both blank and TGF-$\beta_1$ containing beads swelled continuously in PBS to 1.4-times their original size in 120 minutes. After 120 minutes, the beads became so water filled and soft that accurate diameter measurements could not be made. Conversely, TGF-$\beta_1$ containing beads in 0.1 N HCl shrunk to 88% of their original size in 40 minutes. When transferred to PBS (at 120 minutes), the beads exposed to 0.1 N HCl rapidly swelled (but to only 1.1-times their original size) and dissolved.

The results of Examples 1–3 indicate that acid treated beads likely undergo proton-catalyzed hydrolysis or some other transformation that has a positive effect on active drug release from the beads. Although not bound to any particular theory of operation, it is believed that alginate beads in 0.1 N HCl shrink due to the fact that the —COOH groups remain unionized resulting in decreased electrostatic repulsion. However, even at pH 1, the alginate remained very insoluble and the beads retained their sphericity. A consequence of alginate treatment at low pH is increased swelling and dissolution of alginate beads when transferred to neutral pH due to the presence of smaller and more soluble alginate fragments. It was also observed that hydrolysis times in 0.1 N HCl at 37° C. from 0.25–24 hr resulted in no significant differences in the ELISA measured binding activity of TGF-$\beta_1$ (data not shown). In addition, alginate beads treated in 0.1 N HCl at 37° C. for 0.25–24 hr showed little difference in their dissolution profiles and TGF-$\beta_1$ release rates when transferred to PBS, pH 7.4 (data not shown). Accordingly, it appears that acid treatment times of 0.25 hr are sufficient, and that longer treatment times add no benefit in terms of release kinetics and retained immunoreactivity of TGF-$\beta_1$.

Another mechanism which may contribute to the increased release rate of TGF-$\beta_1$ from acid treated beads is that at the pH of the acid treatment (pH 1.0), the carboxylic acid groups remain mostly unionized and no longer interacted with $Ca^{2+}$. Thus, some free $Ca^{2+}$ may diffuse out of the beads resulting in a weaker cross-linked bead which disintegrates faster in pH 7.4. Most likely, the increased release rate of TGF-$\beta_1$ from acid treated beads is due to a combination of proposed mechanisms; that is, acid hydrolysis and reduced calcium cross links. In combination, the mechanisms result in a fast releasing bead made up of smaller alginate fragments held together by weaker calcium cross links.

EXAMPLE 4

Variation of Alginate Molecular Weight

In an attempt to increase the ELISA measured binding of TGF-$\beta_1$, the effect of different molecular weight alginates was investigated. This attempt was made difficult for two reasons. One, alginates having well characterized molecular weights are not commercially available. Typically, alginates having various G/M ratios are available as either low, medium, or high viscosity material. Two, accurate determinations of alginate molecular weights are difficult due to self-association and chemical and physical heterogeneity of the polysaccharide (G. Berth, "Methodical Aspects of Characterization of Alginate and Pectate by Light Scattering and Viscometry Coupled with GPC," *Carb. Poly.* 19:1–9 (1992)).

However, the acid treatment process of alginate beads is considered to be a partial-hydrolysis process that leads to the formation of lower molecular weight alginate. This conclusion is consistent with results in literature (A. Haug et al., "Studies on the Sequence of Uronic Acid Residues in Alginic Acid," *Acta Chem. Scand.* 21:691–704 (1967); A. Haug and B. Larsen, "Quantitative Determination of the Uronic Acid Composition of Alginates," *Acta Chem. Scand.* 16:1908–1918 (1962); A. Haug et al., "The Degradation of Alginates at Different pH Values," *Acta. Chem. Scand.* 17:1466–1468 (1963); A. Haug and B. Larsen, "The Solubility of Alginate at Low pH," *Acta. Chem. Scand.* 17:1653–1662 (1963)). In fact, lower molecular weight alginates due to acid treatment were observed in the gel chromatography studies conducted, but quantification was fraught with difficulties as stated. Other alginates were also investigated for their ability to deliver more active TGF-$\beta_1$ (data not shown). In all cases, the low viscosity, high M ratio (LVM) Sigma product resulted in the formation of beads (especially acid treated beads) which released TGF-$\beta_1$ that was most immunoreactive.

EXAMPLE 5

Immunoreactivity of TGF-$\beta_1$ In Presence of Additives

The immunoreactivity of TGF-$\beta_1$ in solution in the presence of anionic amino acids, polyanions and polycations was studied using the ELISA procedure described in Example 2. To 1 mg/mL solutions of TGF-$\beta_1$ in 5 mM HCl was added from 0 to 0.14%(w/v) of glutamic acid, aspartic acid, poly-L-aspartic acid (PLAA, Mw=13 kDa), sodium carboxymethyl cellulose (Na CMC, high viscosity), or polyacrylic acid (PAA, 2, 90 or 750 kDa). The reactivity of the TGF-$\beta_1$ was then determined by the ELISA procedure, as described in Example 2. The concentrations of the additives studied (up to 0.14% w/v) were analogous to the amount of additive that could be added to the prebead mixture and still have quality beads form. As shown in FIG. 4, as the concentration of additive increased in solution, the percent immunoreactive TGF-$\beta_1$ decreased. Also, the data showed that the lower molecular weight additives such as PLAA, glutamic acid, aspartic acid, and PAA (2 kDa) interfered to a lesser extent with the ELISA measured binding activity of TGF-$\beta_1$. This trend agreed very well with the data from FIG. 2, which shows that TGF-$\beta_1$ had greater immunoreactivity when released from acid treated beads (composed of lower molecular weight alginate) as compared to beads that were not acid treated. Again, greater ELISA measured binding activity reflected reduced interaction between the anionic species and TGF-$\beta_1$.

Evidence for strong stereospecificity between non acid treated alginate and TGF-$\beta_1$ was demonstrated by a comparison of the lowest concentration of alginate (80 kDa) and PAA (90 kDa) that resulted in the highest ELISA measured binding activity of TGF-$\beta_1$. To retain 100% activity of TGF-$\beta_1$, the concentration of alginate had to be less than 0.00015% compared to 0.02% for PAA. Although, both the charge and molecular weight of alginate and PAA were similar, the concentration of alginate needed to interfere with TGF-$\beta_1$ activity was more than 130-times less. These data supported the hypothesis that the interaction of alginate (80 kDa) and TGF-$\beta_1$ (25 kDa) was influenced by both electrostatic and stereospecific interactions. Thus, acid treatment of the alginate beads increased the immunoreactivity of released TGF-$\beta_1$ due to the formation of lower molecular alginate which interacted with the TGF-$\beta_1$ to a lesser extent.

Next, the ability of the additives to shield alginate from TGF-$\beta_1$ in solution was investigated. Alginate solutions were prepared in accordance with the procedure of Example 1, incorporating 50 μg of TGF-$\beta_1$, 0–0.15% (w/v) of sodium alginate and 0.1–1.0 mg (up to 0.125% w/v) of PAA (750 kDa), PLAA (13 kDa), NaCMC high viscosity or glutamic acid. The immunoreactivity of TGF-$\beta_1$ was determined by ELISA as described in Example 2. The concentrations of additives used were chosen based upon the data in FIG. 4 (i.e. the highest concentration of additive not interfering with the immunoreactivity of TGF-$\beta_1$). The results are shown in Table 2:

TABLE 2

| 2% Active TGF-$\beta_1$ | | | | |
|---|---|---|---|---|
| | % Alginate (w/v) | | | |
| Additive | 0 | 0.0015 | 0.015 | 0.15 |
| PAA (750 kDa, 0.0625% w/v) | 34 | 95.3 | 59.19 | 44.68 |
| PLAA (13 kDa, 0.125% w/v) | 99.65 | 77.01 | 53.51 | 28.18 |
| NaCMC (0.0625% w/v) | 5 | 76.7 | 54.02 | 37.5 |
| Glutamic Acid (0.0625% w/v) | 99.6 | 55.38 | 10.78 | 8.95 |
| TGF-$\beta_1$ alone | 100 | 65 | 0 | 0 |

To varying degrees, all additives shielded TGF-$\beta_1$ from alginate with PAA being the most efficient. For example, at a concentration of 0.015% alginate and no additive, TGF-$\beta_1$ had no immunoreactivity. However, upon the addition of 0.0625% PAA, TGF-$\beta_1$ remained nearly 60% immunoreactive.

From the data presented, it was evident that TGF-$\beta_1$ could be shielded from alginate in solution by the addition of PAA or other additives.

EXAMPLE 6

Alginate Beads Containing TGF-$\beta_1$ and Additives

Alginate beads were prepared according to the procedure of Example 1 incorporating 50 $\mu$g TGF-$\beta_1$ and 0.1–1.0 mg of additives. Based upon the results shown in FIG. 4, PAA (750 kDa) and PLAA (13 kDa) were incorporated as potential polyanionic protectants. In addition, Poly-L-Lysine (PLL;123 kDa) was incorporated as a potential polycationic competitor. The additives were incorporated at an alginate:additive w/w ratio of from 75:10 to 75:1 as indicated below in Table 3.

The ELISA measured binding activity of released TGF-$\beta_1$ from beads with additives was determined as described above, and the results are shown in Table 3:

TABLE 3

| % Active TGF-$\beta_1$ Released From Beads | |
|---|---|
| Additive | % Active TGF-$\beta_1$ Released |
| PAA (750 kDa, 75:1) | 19.84 |
| PAA (750 kDa, 75:10) | 0.69 |
| PLAA (13 kDa; 75:10) | 0.73 |
| PLL (123 kDa, 75:1) | 6.92 |
| PLL (123 kDa, 75:5) | 1.14 |
| None | 0.02 |

All alginate beads with either polyanionic or polycationic additives released more immunoreactive TGF-$\beta_1$. The results show that PAA and PLAA performed similarly when incorporated in beads with an alginate to additive ratio of 75:10 (w/w). However, if the PAA incorporated was reduced to 100 $\mu$g (or 75:1 w/w ratio), the immunoreactivity of released TGF-$\beta_1$ was nearly 20%. Actually, the immunoreactivity of released TGF-$\beta_1$ from the 75:1 (w/w) PAA beads was >33% since only 60% of the incorporated TGF-$\beta_1$ was released at the ELISA assay time of 72 hours. The fact that TGF-$\beta_1$ had more immunoreactivity when released from 75:1 (w/w) beads than 75:10 (w/w) was not surprising due to fact that, as demonstrated in FIG. 4, the immunoreactivity of TGF-$\beta_1$ decreased as the concentration of all additives increased. In addition, 75:10 (w/w) beads were somewhat irregular in shape presumably due to interference of PAA with the calcium-alginate crosslinking mechanism. The incorporated polycation, PLL, increased the immunoreactivity of released TGF-$\beta_1$ to a small degree, however, these beads were very irregular as a result of the strong complexation between alginate and PLL.

EXAMPLE 7

Based upon the above results, further studies concentrated on the use of PAA for two reasons. One, the results demonstrated that PAA could increase the ELISA measured immunoreactivity of TGF-$\beta_1$ presumably by shielding alginate from released TGF-$\beta_1$. Two, it would be desirable to have PAA incorporated in the beads since PAA is known to be a strong mucoadhesive (C.M. Lehr et al, "Effects of the Mucoadhesive Polymer Polycarbophil on the Intestinal Absorption of a Peptide Drug in the Rat," *J. Pharm. Pharmacol.* 44:402–407 (1992); D. Duchene and G. Ponchel, "Principle and Investigation of the Bioadhesion Mechanism of Solid Dosage Forms," *Biomaterials* 13:709–714 (1992); J.D. Smart, "An In Vitro Assessment of Some Mucosa-Adhesive Dosage Forms," *Int. J. Pharm.* 73:69–74 (1991)). Therefore, effective targeted delivery of TGF-$\beta_1$ to the enterocytes would be facilitated by localizing the delivery system in the intestinal epithelium due to the formation of bioadhesive bonds.

The ability of high molecular weight PAA (750 kDa) to enhance the immunoreactivity of released TGF-$\beta_1$ was interesting. TGF-$\beta_1$ released from calcium-alginate beads or in the presence of alginate alone had little immunoreactivity. Likewise, TGF-$\beta_1$ in the presence of PAA (750 kDa) had limited activity. However, when PAA was incorporated in alginate beads, the TGF-$\beta_1$ retained more than 33% of its ELISA binding activity. The results obtained suggested that there was a delicate balance between the molecular weight of the components and their concentrations in the beads. For this reason, PAA with molecular weights of 2, 90, 250 and 450 kDa were incorporated in alginate beads at alginate:PAA ratios of 75:1 to 75:10, a portion of the beads was subjected to acid treatment as described above, and the binding activity of released TGF-$\beta_1$ was measured by ELISA. The results are shown in Table 4:

TABLE 4

| Percent Active TGF-$\beta_1$ Released From Beads (%) | | |
|---|---|---|
| PAA Mw (kDa) | Not Acid Treated | Acid Treated |
| 2 kDa (75:1) | 4.2 | 17.5 |
| 90 kDa (75:1) | 12.8 | 16 |
| 90 kDa (75:6) | | 79 |
| 90 kDa (75:10) | | 81 |
| 250 kDa (75:1) | 2.1 | |
| 450 kDa (75:1) | 2.1 | |

Acid treated beads containing PAA (90 kDa) with alginate to PAA ratios of 75:6 (w/w) and 75:10 (w/w) were able to deliver TGF-$\beta_1$ with 80% immunoreactivity. In addition, as the concentration of PAA was increased in the acid treated beads from 100 $\mu$g (75:1 w/w beads) to 600 $\mu$g (75:6 w/w beads), the immunoreactivity of released TGF-$\beta_1$ increased dramatically. This was opposite to the results shown in Table 3. Again, the results suggested a fine balance between the molecular weights and concentrations of both PAA and alginate. It was also interesting to note the physical state of cured alginate beads with PAA. As the molecular weight of the PAA incorporated increased, the beads became more irregular. This was especially true at higher concentrations of 250 and 450 kDa PAA.

EXAMPLE 8

Figure 5:
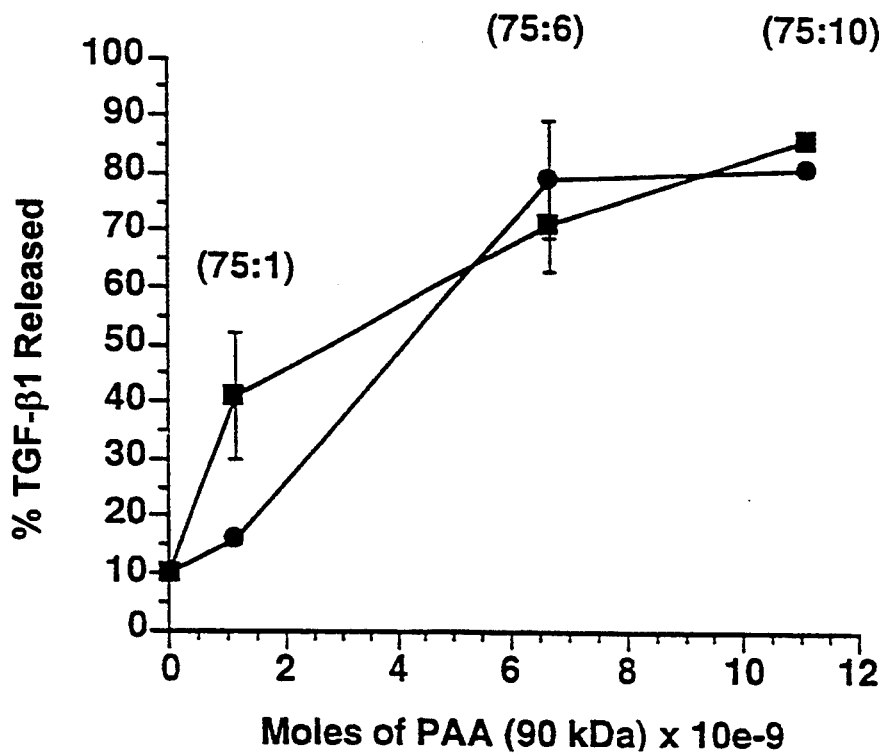
FIG. 5 is a graphical representation of ELISA measured binding activity of released TGF-$\beta_1$, available in immunoreactive form, from alginate beads at 37° C. in PBS, pH 7.4 as a function of moles of PAA (90 kDa) added. Incubation time of PAA and TGF-$\beta_1$ prior to adding alginate, curing in 1% CaCl$_2$ for 10 minutes, and acid treatment in 0.1 N HCl at 37° C. for 30 minutes was: 5 minutes (shown as ■ in FIG. 5); and 60 minutes (shown as ● in FIG. 5). Absolute amount of immunoreactive TGF-$\beta_1$ released was assayed at 2 hr.

To further assess the effect of amount of PAA incorporation on immunoreactivity of released TGF-$\beta_1$, alginate beads were prepared by incubating TGF-$\beta_1$ and PAA (90 kDa) for either 5 or 60 minutes (see FIG. 7) in w/w ratios of 75:1, 75:6 and 75:10, followed by dilution, addition of alginate, and bead formation in 1% $CaCl_2$. The beads were acid treated in 0.1 N HCl at 37° C. for 30 minutes and then incubated at 37° C. in PBS, pH 7.4. After 2 hours, the immunoreactivity of released TGF-$\beta_1$ was determined by ELISA as described in Example 2. The results are shown in FIG. 5, in which (■) represents TGF-$\beta_1$ and PAA incubation for 5 minutes while (●) represents the 60 minute incubation. As shown in FIG. 5, there was little difference between 5 and 60 incubation times for PAA and TGF-$\beta_1$. However, a positive correlation existed between the amount of PAA added and the ultimate immunoreactivity of the released TGF-$\beta_1$. No significant difference is seen with the 75:6 (w/w) and 75:10 (w/w) beads suggesting that no advantage is obtained using alginate to PAA ratios greater than 75:6 (w/w). However, higher concentrations of PAA may be useful in increasing bioadhesiveness of the beads. At alginate:PAA ratios greater than 75:10, bead formation becomes difficult.

EXAMPLE 9

Figure 6:
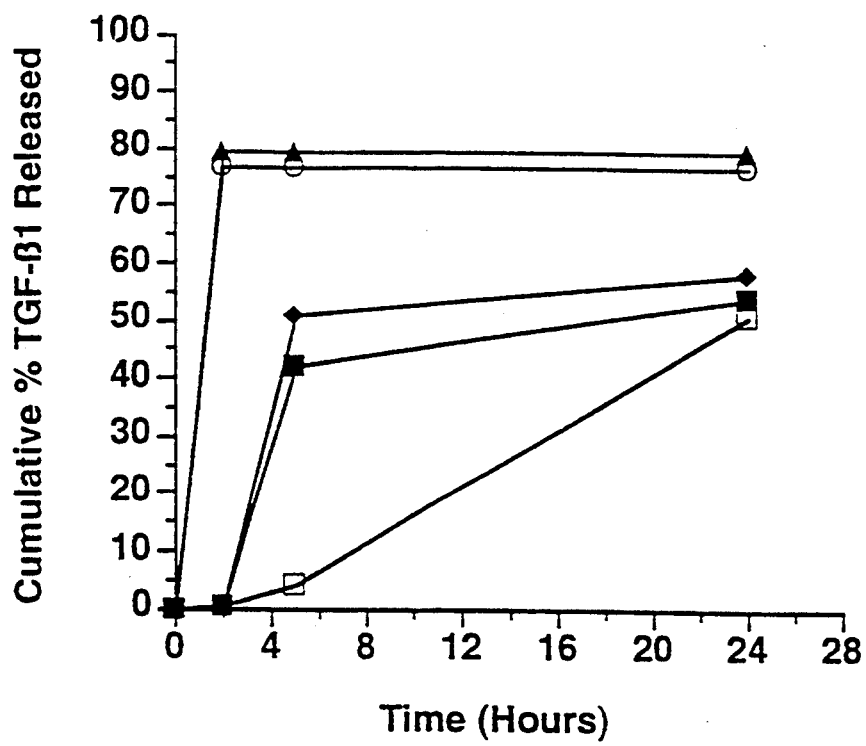
FIG. 6 is a graphical representation of ELISA measured binding activity of released TGF-$\beta_1$, available in immunoreactive form, from alginate beads (75:6 w/w) with PAA (90 kDa) at 37° C. in PBS, pH 7.4. Beads were acid treated in pH 1 (shown as ▲ in FIG. 6), pH 2 (○), pH 3 (■), pH 4 (◆) or pH 7 (□) for 30 minutes at 37° C. as described in Example 8. Absolute amount of immunoreactive TGF-$\beta_1$ released was assayed at the times shown in FIG. 6.

To determine the effect of acid treatment, preparations of alginate beads with PAA as an additive were made by the incubation of PAA with TGF-$\beta_1$, followed by dilution, the addition of alginate, and the formation of beads as described in Example 1. The beads were acid treated by incubation for 30 minutes at 37° C. at a pH of from 1–7, and the immunoactivity of released TGF-$\beta_1$ was determined by ELISA as described above. In FIG. 6, the ELISA measured cumulative binding activity of released TGF-$\beta_1$ from acid treated beads was determined as a function of the pH of the hydrolysis medium. As expected, alginate beads treated at pH 1 (▲) and pH 2 (◯) release 80% immunoreactive TGF-$\beta_1$ within 2–3 hours as measured by ELISA. In fact, these beads rapidly swelled and completely dissolved due to the presence of lower molecular weight alginate fragments. In comparison, the alginate beads treated at pH 3 (■), pH 4 (◆), and pH 7 (□) released TGF-$\beta_1$ at a reduced rate and with less immunoreactivity. As the pH of the treatment solution was increased, the extent of release of immunoactive TGF-$\beta_1$ was reduced. Therefore, a larger fraction of higher molecular weight alginate was retained in beads exposed to higher pH and as a result, the beads remained intact longer and the interaction between TGF-$\beta_1$ and alginate was enhanced. The pH at which the beads were treated also affected the TGF-$\beta_1$ release rate. Beads treated at a low pH (between 1 and 2) released the TGF-$\beta_1$ within 2–3 hours. As the pH of treatment solution was increased the TGF-$\beta_1$ release time also increased.

EXAMPLE 10

Alginate beads containing TGF-$\beta_1$ and 90 kDa PAA (75:10 w/w in alginate:PAA) were prepared following the procedure of Example 1, and were acid treated for 30 minutes at 37° C. in 0.1 N HCl, as described in Example 2. The beads were then placed in PBS, pH 7.4, and the immunoreactivity of released TGF-$\beta_1$ was determined by $^{125}I$ radiolabel and ELISA, as described in Example 2. In addition, a growth inhibitory assay (GIA) was used to determine the bioactivity of the TGF-$\beta_1$. The GIA measures the ability of TGF-$\beta_1$ to inhibit the growth of mink lung epithelial cells (ATCC #CCL64) (T. Ikedaet al., "Human Transforming Growth Factor Type $\beta$2: Production By a Prostatic Adenocarcinoma Cell Line, Purification and Initial Characterization," *Biochemistry* 26:2406–2410 (1987)). The activity of the growth factor was determined by the inhibitory response of the cells to different concentrations of TGF-$\beta_1$. Cell viability was based on the enzymatic cleavage by metabolically active cells of a tetrazolium salt into an orange/red formazan product. Prior to the assay cells were trypsinized and plated in a 96-well flat bottomed plate (Costar) at a concentration of 1000 cells/well. After allowing the cells to attach, samples containing the TGF-$\beta_1$ and a reference standard were diluted to concentrations ranging from 1000 to 1.95 pg/ml and added to the wells. The cells were incubated for four days after which time a 100 $\mu$L solution containing 25 $\mu$g of sodium 3"-[1-(phenylamino)-carbonyl]-3,4-tetrazolium-bis(4-methoxy-6-nitro) benzene sulfonic acid hydrate (Diagnostic Chemicals, Ltd.) and 5 mM phenazine methosulfate (Aldrich) in media was added to each well. The cells were then incubated for 7 hours and the plates read on a microplate reader at an absorbance of 450 nm with a 630 nm reference filter. The specific activity of a sample was calculated relative to the reference material.

Figure 7:
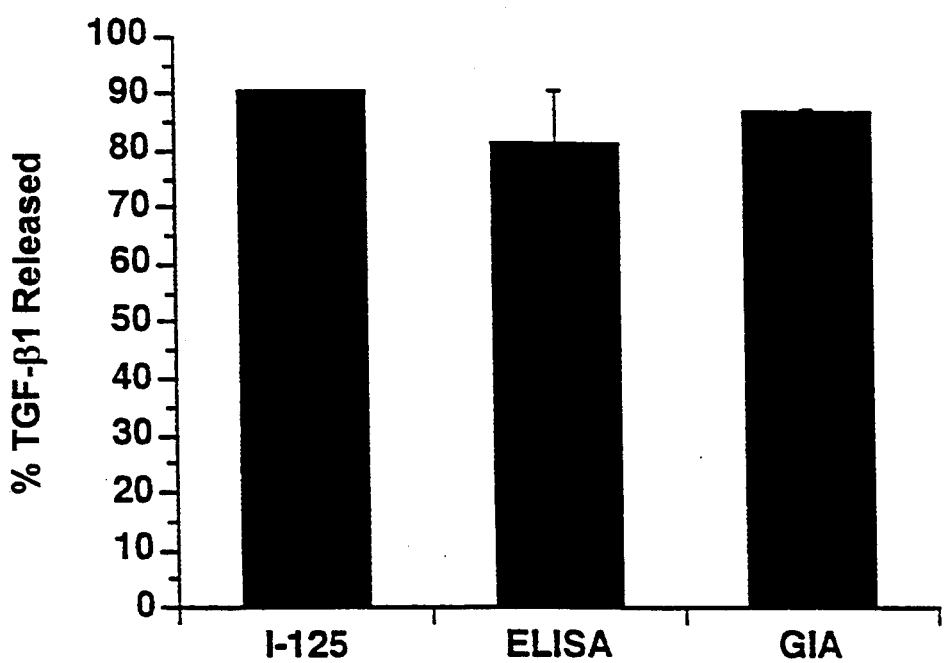
FIG. 7 is a graphical representation of percent TGF-$\beta_1$ released from alginate beads (75:10 w/w) with PAA (90 kDa) at 37° C. in PBS, pH 7.4 as measured by: $^{125}$I (total released TGF-$\beta_1$), ELISA (total released TGF-$\beta_1$ available in immunoreactive form), and growth inhibition assay (GIA) bioassay (total released TGF-$\beta_1$ in bioactive form). Beads were acid treated in 0.1 N HCl for 30 minutes at 37° C.

The results are shown in FIG. 7. As measured by $^{125}I$ radiolabel, a total release of 90% of the TGF-$\beta_1$ was obtained. As measured by ELISA, over 80% of the TGF-$\beta_1$ was released and immunoreactive. The GIA results indicate that more than 85% of TGF-$\beta_1$ was bioactive.

Alginate beads containing TGF-$\beta_1$ were prepared following the procedure of Example 1, which: A. contained no PAA or other additives and were not acid treated (analogous to the condition of FIG. 1A); B. contained no PAA, and were acid treated in 0.1 N HCl at 37° C. for 30 minutes (analogous to the condition of FIG. 1B); C. contained 90 kDa PAA (75:6 w/w in alginate:PAA) and were not acid treated (analogous to the condition of FIG. 1C); or D. contained PAA as described in C., and were acid treated as described in B. The total percentage of immunoreactive TGF-$\beta_1$ was determined for each sample by ELISA as described in Example 2, and the results are shown in Table 5. As seen in Table 5, the combination of PAA protection and acid treatment results in the highest release of immunoreactive TGF-$\beta_1$.

TABLE 5

| Beads | Percentage Immunoreactive TGF-$\beta_1$ Released (%) |
|---|---|
| A | 0.01 |
| B | 8.2 |
| C | 50.8 |
| D | 82.4 |

Figure 8:
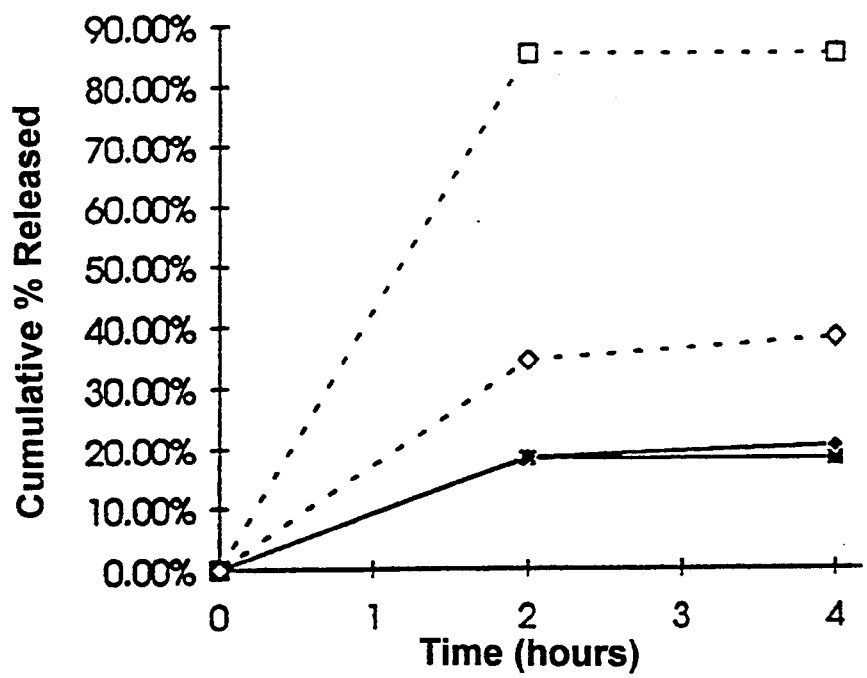
FIG. 8 is a graphical representation of the percentage of total Oncostatin-M released in immunoreactive form, as measured by ELISA, from alginate beads as described in Example 11, in which (□) represents acid treated beads containing PAA, (◆) represents bead containing PAA which were not acid treated, (■) represents beads without PAA which were acid treated, and ◆ represents beads without PAA which were not acid treated, as described in Example 11.

EXAMPLE 11

Following the procedure of Example 1, alginate beads were prepared from 800 $\mu$l of an aqueous solution containing 25 $\mu$g of Oncostatin-M (site source) and 3750 $\mu$g of sodium alginate (Sigma, Low Viscosity). To a portion of the solution was added 300 $\mu$g of PAA (Jannsen, 90 kDa) prior to bead formation. Samples of the beads, both with and without added PAA, were subject to acid treatment by incubating the beads in 0.1 N HCl at 37° C. for 30 minutes, as described in Example 2. The beads were then placed in PBS, and the percentage amount of immunoreactive Oncostatin-M was determined by ELISA assay following the procedure of Example 2 using a mouse anti-Oncostatin-M antibody, 11R2 (Bristol-Myers Squibb, Seattle, WA) as the capture antibody and biotinylated 1R10 mouse anti-Oncostatin-M antibody (Bristol-Myers Squibb, Seattle, WA) as the probe, followed by horseradish peroxidase/avidin D. The results are shown in FIG. 8, in which (□) represents acid treated beads containing PAA, ( ) represents bead containing PAA which were not acid treated, (■) represents beads without PAA which were acid treated, and ♦ represents beads without PAA which were not acid treated. As shown in FIG. 8, acid treated beads containing PAA rapidly released 85% immunoreactive Oncostatin-M compared with 38% release from non acid treated beads containing PAA, 20% from non acid treated beads with PAA and 18% from acid treated beads without PAA.

EXAMPLE 12

Figure 9:
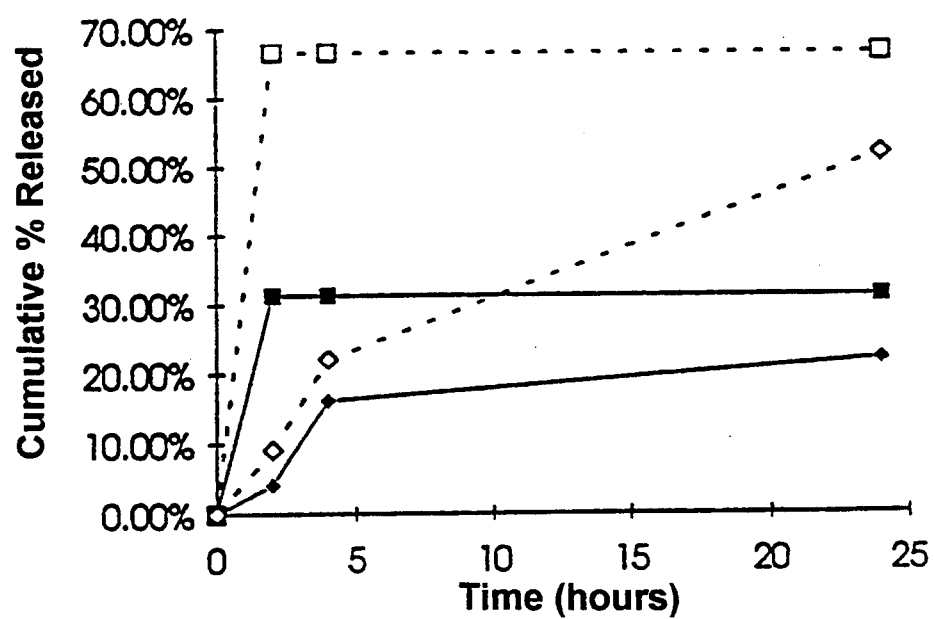
FIG. 9 is a graphical representation of the percentage of total Amphiregulin released in immunoreactive form, as measured by ELISA, from alginate beads as described in Example 10, in which the symbols have meanings corresponding to those in FIG. 8.
Figure 10:
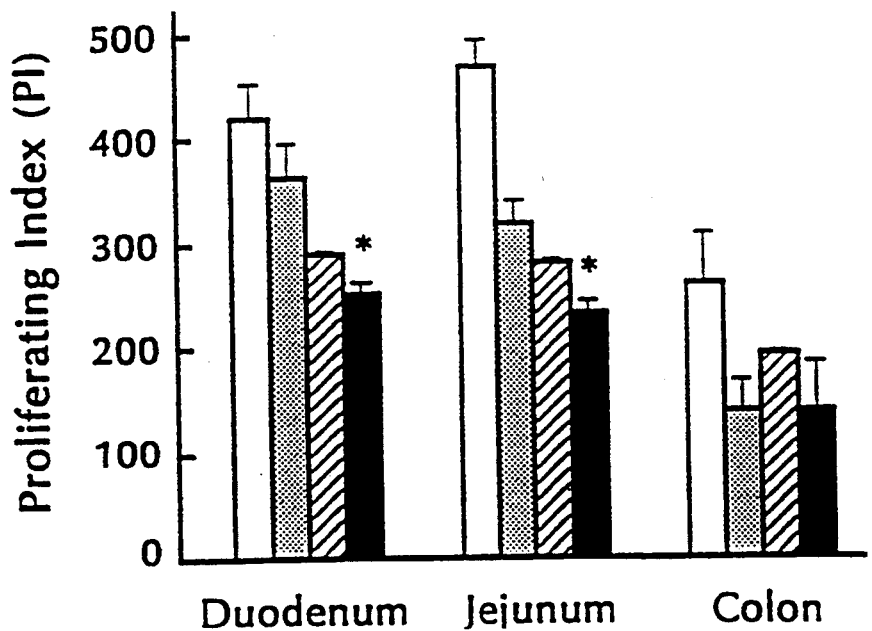
FIG. 10 is a graphical representation of the proliferating index (PI) of cells from duodenum, jejunum and colon tissue samples taken from Sprague-Dawley rats treated with no TGF-$\beta_1$ (open bar in FIG. 10), intraperitoneal TGF-$\beta_1$ (half-tone bar), peroral TGF-$\beta_1$, in phosphate buffered saline (cross-hatched bar) or TGF-$\beta_1$ in alginate beads (solid black bar), as described in Example 13.

The procedure of Example 10 was repeated substituting 25 µg of Amphiregulin for the Oncostatin-M of Example 11 and using a mouse antiamphiregulin monoclonal antibody, 6R1C1 (Bristol-Myers Squibb, Seattle, WA) as the capture antibody, followed by a goat antimouse horseradish peroxidase probe (Southern Biotech). The results are shown in FIG. 9 in which the symbols have the meanings of FIG. 8. As shown in FIG. 10, 67% of immunoreactive Amphiregulin was released from acid treated beads containing PAA, compared with 52% release from non acid treated beads containing PAA, 31% release from acid treated beads without PAA and 22% release from non acid treated beads without PAA.

EXAMPLE 13

Adult male Sprague-Dawley rats (250±30 g) were caged individually and handled according to the guidelines of American Association for the Accreditation of Laboratory Animal Care (AAALAC). For peroral administration of TGF-$\beta_1$, the rats were anesthetized with intramuscularly injected ketamine-HCl (40 mg/kg) (Vetalar®, Aveco Inc., Fort Dodge, Iowa) and a catheter was inserted into the stomach perorally to exclude the failure of the formulation to reach stomach and intestine. Intraperitoneal injections were performed into the lower right quadrant of the abdomen. Based on preliminary studies on dose, treatment time and route of administration of TGF-$\beta_1$ (data not shown), the animals were divided into four groups (5–6 rats per group) and were treated as follows: 1) TGF-$\beta_1$ in alginate beads prepared in accordance with Example 7 perorally (P.O.) (25 µg once a day for 5 days); 2) TGF-$\beta_1$ in PBS P.O. (25 µg once a day for 5 days); 3) TGF-$\beta_1$ in PBS intraperitoneally (I.P.) (12.5 µg twice a day for 10 days); 4) control animals received 1 ml of PBS P.O. or I.P. After treatment of 5 or 10 days the rats were sacrificed with an overdose of the anesthetic. The intestine was removed and the lumen flushed with cold PBS. Segments (approximately 10% each of total length) were removed from duodenum, jejunum, ileum and colon. The gut was opened longitudinally, attached to hard paper with needles to maintain unaffected morphology, fixed in Met Carnoys fixative (60% methanol, 30% chloroform, 10% acetic acid) overnight and changed into 70% ethanol. Tissue was embedded in paraffin and cut to 5 µm sections with a microtome. Samples were then stained with hematoxylin eosin for histomorphological analysis or prepared for immunohistochemical studies. A marked reduction in villus height (50–70%) was observed in the duodenum and jejunum of animals that received TGF-$\beta_1$ perorally in alginate beads.

Cell proliferation was quantified using immunohistochemical techniques for detecting proliferating cell nuclear antigen (PCNA), an endogenous marker of proliferating cells. Positive staining for PCNA was judged based upon cellular distribution and intensity of the brown to black reaction product that correlated with the different phases of cell cycle. The proliferating index (PI) was calculated as the number of epithelial cells in G1, S, G2 or M phase of the cell cycle per length (ram) of crypts counted. Four 0.25 mm areas (1 mm total) were scored for cell proliferation. The results are shown in FIG. 10. The PI was significantly reduced ($p<0.05$) in the duodenum and jejunum of animals that received TGF-$\beta_1$ in alginate beads perorally.

Figure 11:
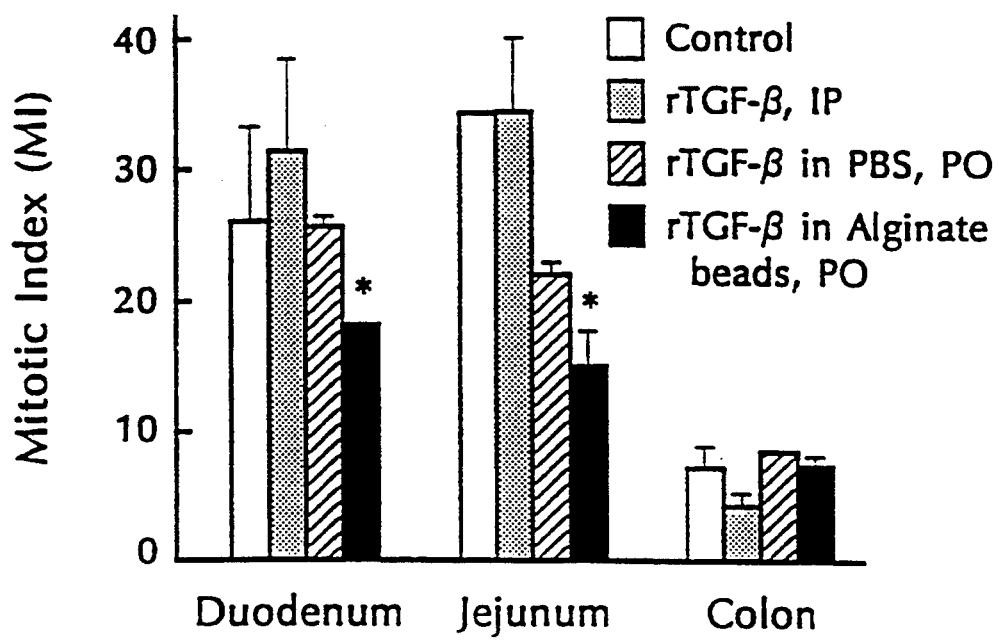
FIG. 11 is a graphical representation of the mitotic index of the cells from the tissue samples of FIG. 10, as described in Example 13.

The mitotic index (MI) was determined as the number of mitotic figures per mm in the same fields scored for PI. The cell proliferation data were analyzed statistically using the Student's t-test for inquity of unpaired data sets between treated and control animal groups. The 5% significance level was used as the criterion for statistical significance. The results are shown in FIG. 11. The MI was significantly reduced ($p<0.05$) in the duodenum and jejunum of animals that received TGF-$\beta_1$ in alginate beads perorally.

In controls, high amounts of PCNA-staining corresponding to marked cellular proliferative activity was seen. In animals treated with TGF-$\beta_1$ I.P. or P.O. in PBS moderate staining was present. In TGF-$\beta_1$ alginate beads treated animals only minimal staining was found indicating quiescence of the crypt stem cells.

It is apparent from the foregoing that alginate-calcium beads can be used as an effective oral delivery system for cationic therapeutic agents in accordance with the practice of the present invention. TGF-$\beta_1$ released from beads alone had no binding activity as measured by ELISA. However, the addition of PAA as an polyanionic additive coupled with acid treatment led to the retention of high TGF-$\beta_1$ binding activity. The pH of the alginate bead treatment may be used to control the release rate of TGF-$\beta_1$ from the beads. Prepared alginate beads containing TGF-$\beta_1$ and PAA can be exposed to a controlled acid treatment process, isolated, lyophilized, and encapsulated in a hard gelatin capsule for oral delivery. In use of the capsules, no TGF-$\beta_1$ is released in the pH 1 environment of the stomach, however, at pH 7 in the intestines, active and PAA protected TGF-$\beta_1$ would be released linearly over 2–3 hours. In addition, PAA can serve as a bioadhesive providing targeted delivery of TGF-$\beta_1$ to enterocytes of the intestine.

The embodiments of the invention in which an exclusive property or privilege is claimed are defined as follows:

1. A sustained release composition comprising a cationic therapeutic agent, a multivalent cation crosslinked alginate, and a weight/weight ratio of from about 75:2 to 75:10 based on the weight of alginate of a polyacrylic acid having a molecular weight of about 50 to 150 kDa, wherein the alginate has been crosslinked in the presence of the therapeutic agent and the polyacrylic acid to obtain a sustained release composition capable of releasing the cationic therapeutic agent in active form.

2. The composition of claim 1 which comprises a weight/weight ratio of from about 75:6 to about 75:10 based on the weight of alginate of a polyacrylic acid having a molecular weight of about 75 to 100 kDa.

3. The composition of claim 1 wherein the alginate has been incubated at a pH less than about 2.

4. The composition of claim 1 wherein the therapeutic agent is selected from the group consisting of TGF-$\beta_1$, Oncostatin-M and Amphiregulin.

5. A sustained release composition comprising TGF-$\beta_1$, calcium ion crosslinked alginate, and a weight/weight ratio of from about 75:6 to 75:10 based on the weight of alginate of a polyacrylic acid having a molecular weight of about 75 to 150 kDa, said alginate having been crosslinked in the presence of the TGF-$\beta_1$ and the polyacrylic acid, and then incubated at a pH less than about 2 to enhance the release of TGF-$\beta_1$ from the composition in active form.

6. A method of preparing alginate beads for the oral delivery of a therapeutic agent to a human or nonhuman mammal in need thereof, comprising forming a mixture of the therapeutic agent, an anionic polyacrylic acid protective polymer and alginate, introducing drops of the mixture into a solution of a multivalent cation to crosslink the alginate and form the beads, and then incubating the beads at acid pH for a time sufficient to enhance release of the therapeutic agents from the beads.

7. The method of claim 6 wherein the mixture comprises a weight/weight ratio of from about 75:2 to about 75:10 based on the weight of alginate of a polyacrylic acid having a molecular weight of about 75 to 100 kDa.

8. The method of claim 6 wherein the beads are incubated at a pH less than about 2.

9. The method of claim 8 wherein the beads are incubated at a pH of about 1 for at least about 15 minutes.

10. The method of claim 6 wherein the therapeutic agent is selected from the group consisting of TGF-$\beta_1$, Oncostatin-M and Amphiregulin.

* * * * *